Feb. 22, 1949. G. C. SPARRE Plant Pat. 825
CHRYSANTHEMUM PLANT
Filed June 19, 1947
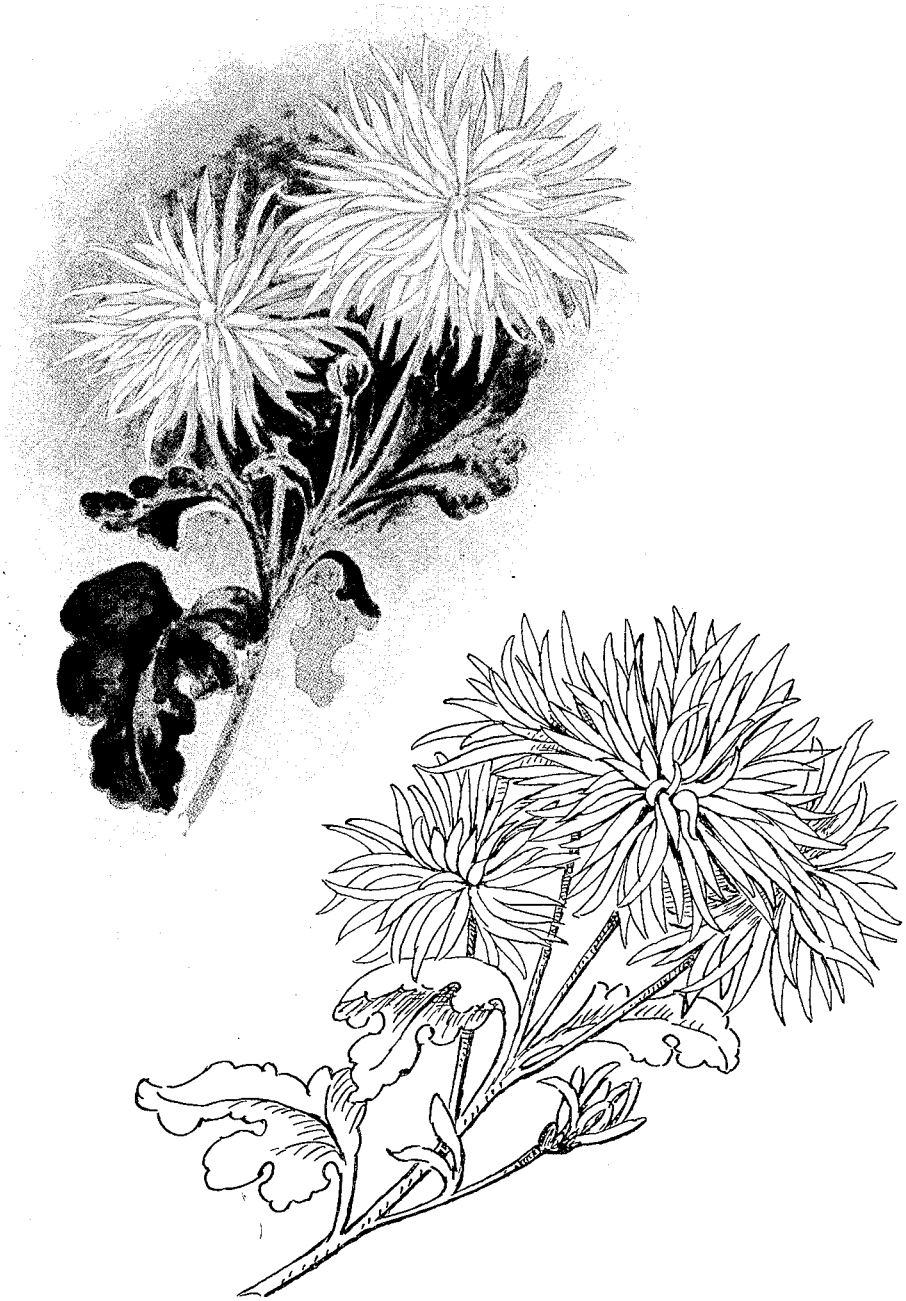
WITNESS
Addison F. Avery
INVENTOR
Gustav C. Sparre,
by: John Harrow Kennard
his ATTY Patented Feb. 22, 1949

Plant Pat. 825

UNITED STATES PATENT OFFICE

825

CHRYSANTHEMUM PLANT

Gustav C. Sparre, Clarkson, Ontario, Canada, assignor to John J. Grullemans, Mentor, Ohio Application June 19, 1947, Serial No. 755,681

1 Claim. (Cl. 47—60)

This invention relates to a new and distinct variety of chrysanthemum plant.

The drawing shows in one view, in color, the terminal of one of the main stalks with the terminal inflorescence and leaves and a similar view in black and white indicating the structure in more detail.

The new variety was produced by me by crossing a chrysanthemum known as Mrs. Dunnington Grubb, as the seed parent, with the chrysanthemum known as the Snowbird, as the pollen parent, both the seed parent and pollen parent being crosses between *Chrysanthemum indicum* and a Korean strain. The new variety was first produced by me in my gardens at Clarkson, Ontario, Canada and was first there asexually reproduced by root cuttings of the original. Additional cuttings of the original plant were asexually reproduced in the fields of The Wayside Gardens Company, of Mentor, Ohio, and both they and the original are still growing.

The plant has fibrous, massed roots of medium size for this type of plant. The roots are rather shallow and of the usual spread, being about equal to the spread of the upper or exposed portion of the plant. The resistance of the roots to disease, wetness and drought is good as also are their winter resistance. Unprotected, they have withstood temperatures of from 12° to 15° below zero (F.). The plant thrives well in the usual types of soil adapted for chrysanthemums.

The exposed plant has the usual herbaceous characteristics, being generally upright and medium compact. A one year old plant averages in height about eighteen to twenty inches with a spread of about eighteen to twenty-four inches. Two to three year old plants average about thirty-six inches in height. The exposed plant is generally oval in shape and of vigorous growth. Its resistance to low temperature, both protected and unprotected, is good for that type of plant, as also is its resistance to disease, drought and wetness. It prefers moderate sun and any exposure except north and thrives in any good garden loam under the usual conditions suitable to chrysanthemums, preferring a well drained soil.

The main stalks are upright, herbaceous and very much branched. For this type of plant they are relatively stiff but are generally adequate to support the foliage and bloom well and have a tendency toward brittleness. The color of the main stalks is generally dark green on both the new and old growth and is quite uniform. The length of the main stalks averages from thirty to thirty-six inches on a two year old plant, the surface texture being smooth and the main stalks being generally divergent from the roots. The branches are whorled and of dark green color and hirsute surface texture.

The foliage is best described as loose with an abundance of leaves in whorled arrangement. The leaves generally are a dull green on top, comparable to Maerz and Paul Plate 16–L–5 and a lighter green on the bottom, comparable to Maerz and Paul Plate 22–H–4. Quite generally they have brown areas, comparable to Maerz and Paul Plate 56–H–4. The color is generally uniform. The leaf size and shape is usual for the type of plant, the leaves being of a medium thickness with hirsute upper and lower faces. Their persistency on the plant is excellent. The petioles or leaf stems are of average length, dull green in color with a smooth surface texture and of medium strength.

The plant is suitable for growing throughout the entire United States and bears blooms of good quality and in large quantity in substantially any location. For the best blooming, it prefers a sunny southern exposure with a reasonably moist, fairly cool season. It blooms best in well drained but moist, neutral soil. It prefers a rich sandy loam. The quality and quantity of the blooms are best when there is at least a half day's sun with cool weather and a fairly moist soil but the color is not particularly affected by changed conditions of exposure and soil. Excessive heat and shade appears to reduce the size of the bloom only. The plant blooms usually throughout September but sometimes also the latter part of August, the blooming period being continuous. The blooms are persistent on the plant and the blooming period is lengthened by removal of old flowers.

The buds are of the usual globular form and are borne in an upright position. Their color, when the sepals first divide, is pure white which continues as the petals begin to unfurl. By the time the bloom is half blown the pure white continues except for a tendency toward a green color toward the center. When in full bloom the flowers are white comparable to Maerz and Paul Plate 10–A–1, with the deeper shadows comparable to Maerz and Paul Plate 10–D–1. An occasional outer petal is edged with a pale lilac, comparable to Maerz and Paul Plate 41–I–5.

The blooms are full double, of an average diameter of three to four inches. The average plant bears from thirty to fifty blooms which are borne in heads or clusters of three or four to a stem. The blooms are very persistent and long lasting. The individual petals vary from a creamy white at the center of the flower to a pure white outwardly therefrom, the base of the petals being a greenish white. The reverse of the petals is a pure white so that the general tonality of the blooms from a distance is white. There is practically no change in color during the blooming season except that after the blossoms are several days old, the reverse of the petals flushes with a pale lilac.

The petals are smooth and waxy, both inside and outside. They are generally lanceolate but very narrow, being sharply pointed at both ends. They are arranged similar to those of a cactus dahlia but are not imbricated. The blooms the shaggy, fully double, and generally globular and very graceful in appearance. There are no petaloids in the center. They have a faint chrysanthemum fragrance.

The stamens are generally composite and the fruit is usual in shape but insignificant and sparse.

Another special characteristic of the plant is that the flowers are produced in open clusters which permits a fine showing of their details.

Each of the characteristics of the plant mentioned herein and the combinations of part or all thereof, I claim distinguish the new variety from all other known varieties of chrysanthemum plants.

I claim:

The new variety of chrysanthemum plant herein shown and described characterized in that its flowers are fully double, are shaped like the flowers of a cactus dahlia, are large yet very graceful in appearance and of an exceptional whiteness and are produced in open clusters, and the plant is exceedingly vigorous, has the ability to withstand severe winters, whether protected or unprotected, is exceptionally resistant to disease, and has good resistance to drought.

GUSTAV C. SPARRE.

(No references cited).